US008670940B2

(12) United States Patent
Hirose et al.

(10) Patent No.: US 8,670,940 B2
(45) Date of Patent: Mar. 11, 2014

(54) PLANT INFORMATION MANAGEMENT SYSTEM AND PLANT INFORMATION MANAGEMENT METHOD

(75) Inventors: Yoshitsugu Hirose, Tokyo (JP); Shaoyang Lin, Kisarazu (JP); Atsushi Sasaki, Futtsu (JP)

(73) Assignee: Honda Motor Co., Ltd., Tokyo (JP)

( * ) Notice: Subject to any disclaimer, the term of this patent is extended or adjusted under 35 U.S.C. 154(b) by 1259 days.

(21) Appl. No.: 12/180,897

(22) Filed: Jul. 28, 2008

(65) Prior Publication Data

US 2009/0222487 A1 Sep. 3, 2009

(30) Foreign Application Priority Data

Feb. 28, 2008 (JP) ................................. 2008-048124

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................... 702/19; 702/22; 703/11; 703/12

(58) Field of Classification Search
None
See application file for complete search history.

(56) References Cited

U.S. PATENT DOCUMENTS

2003/0028914 A1 * 2/2003 Liu et al. ....................... 800/278

FOREIGN PATENT DOCUMENTS

| | | | |
|---|---|---|---|
| JP | 07-334569 | A | 12/1995 |
| JP | 2001-061342 | | 3/2001 |
| JP | 2001-078575 | | 3/2001 |
| JP | 2001-222520 | A | 8/2001 |
| JP | 2002-007602 | | 1/2002 |
| JP | 2004-512007 | | 4/2004 |
| JP | 2005-031757 | A | 2/2005 |
| JP | 2006-115768 | A | 5/2006 |
| JP | 2006-146570 | A | 6/2006 |
| WO | WO 01/64926 | A2 | 9/2001 |

OTHER PUBLICATIONS

Jayashree et al. (BMC Bioinformatics 2006, 7:383).*
Kumagai et al. (Plant Molecular Biology (2006) 61:515-523).*
Chang et al. (Taichung District Agricultural Improvement Station Research Report, vol. 21, p. 15-22, 1988, machine translation provided).*
Notice of Reasons for Rejection issued Nov. 13, 2012, in counterpart Japanese Patent Application No. 2008-048124 (6 pages including English translation).
Takeya, Masaru, et al., "Image Data Management of Plant Genetic Resources Database System," IPSJ SIG Notes, Information Processing Society of Japan, Jan. 27, 1995, vol. 95, No. 12, pp. 137-143 (14 pages total including English translation).
Office Action issued to JP Application No. 2008-048124 issued on Apr. 24, 2012.

* cited by examiner

*Primary Examiner* — Larry D Riggs, II
(74) *Attorney, Agent, or Firm* — Arent Fox LLP

(57) ABSTRACT

A plant information management system comprising: a seed identification information input device; an individual plant identification information retrieval device; an individual plant identification information input device; a new seed identification information retrieval device; a storage location information retrieval device; a project database management device; a seed database management device; a project database memory device; and a seed database memory device.

12 Claims, 13 Drawing Sheets

FIG. 2

| PROJECT NAME | | |
|---|---|---|
| SEED 1 | NAME | |
| | AMOUNT | |
| | LOCATION | |
| SEED 2 | NAME | |
| | AMOUNT | |
| | LOCATION | |
| INDIVIDUAL PLANT 1 | NAME | |
| | LOCATION | |
| INDIVIDUAL PLANT 2 | NAME | |
| | LOCATION | |
| ⋮ | ⋮ | |
| MATING 1 | FEMALE | |
| | MALE | |
| | OFFSPRING | |
| MATING 2 | FEMALE | |
| | MALE | |
| | OFFSPRING | |
| ⋮ | ⋮ | |
| PROCEDURE | SEED SOAKING | |
| | SEED PLANTING | |
| | ⋮ | |

PLANT INFORMATION MANAGEMENT SYSTEM AND PLANT INFORMATION MANAGEMENT METHOD

BACKGROUND OF THE INVENTION

Priority is claimed on Japanese Patent Application No. 2008-048124, filed Feb. 28, 2008, the contents of which are incorporated herein by reference.

FIELD OF THE INVENTION

This invention relates to a plant information management system and a plant information management method.

DESCRIPTION OF RELATED ART

The term cultivar is defined as: subgroup of organisms belonging to one species, having difference in particular characteristics from the rest of the individuals of the same species, the difference derived from certain difference in genetic constitution. That is, even for plants belonging to the same species, depending on the cultivar, there are difference in characteristics including readiness of the cultivation, resistance to damage from pests or insects, yields, and produce qualities. Accordingly, there is a long history of breeding in order to obtain cultivars with superior characteristics, for important field crops including wheat and rice. In recent years, breeding have been carried out not only by companies handling seeds and seedlings, but also by public institutions, including national and local institutions. Not only for food plants, but also for gardening plants, breeding for new cultivars having various colors and forms have been actively carried out, in response to diverging demands of consumers in recent years. These days, plant resources have been gaining more attention for their use as a source of biomass ethanol, and new cultivars are desired for superior resource behavior for this purpose.

In many plants, reproduction of individual plants can be easily carried out by the virtue of plant seeds. Accordingly, the preservation and management of seeds is quite important in the development of new cultivars. In particular, since seeds of the same species have virtually the same shape, it is practically impossible to distinguish seeds of different cultivars by the appearance of the seeds. Accordingly, if seeds of different cultivars are accidentally mixed, it is required to sow the seed, cultivate it, and confirm whether or not the unique characteristics of the cultivar appear in the plant, in order to specify the cultivar of particular one of mixed seeds. To avoid mixing up of the seeds, appropriate seed preservation and management methods are required. Accordingly, an efficient and easy to use management system has been desired.

For appropriate seeds management, it is necessary, not only to preserve seeds, but also to identify and manage individual plants cultivated from the seeds, because next-generation seeds are harvested from the individual plants. In particular, in test farms which are managed for the purpose of obtaining novel cultivar, when plants of different cultivars are cultivated in the same field, or when an extensive amounts of different cultivars are cultivated in one project, management of individual plants becomes particularly important.

When plants are cultivated, in order to identify the cultivated plant, labels, e.g., tags containing information on the plant are attached to the plants. In the conventional methods, the information on the labels is manually prepared, causing frequent mislabeling and misunderstanding. Therefore, there are problems in that frequent errors in identifying and cropping individual plants of the cultivar occur.

In view of the above problems, a new system will contribute largely to cultivar development, which can perform management of fields and plant seeds, by identifying each individual plant cultivated in the field, and prevent errors in identification of cultivar in the process of the cultivation and the analysis of each individual plant.

A number of systems and methods have been disclosed for managing plants and fields. For example, (1) a crop quality management system is disclosed, which can perform management of product quality control information, including records of fertilization and insect/weed prevention (for example, refer to Japanese Unexamined Patent Application, First Publication No. 2005-31757). Also, (2) an individual plant identification/tracking system is disclosed, which can track harvested crops, and confirm that the harvested crop and the purchased crop are identical, by using: meteorological observations at a plurality of points in the managed culture field for the cultivated crop; and field servers provided in order to collect and monitor culture environment data (for example, refer to Japanese Unexamined Patent Application, First Publication No. 2006-146570). Furthermore, (3) a plant management method is disclosed, which is characterized by the method identifying individual plants by attaching IC tags to the plant body (for example, refer to Japanese Unexamined Patent Application, First Publication No. 2006-115768).

However, although the aforementioned systems (1) and (2) can manage field characteristics of fields including soil conditions, those systems can not identify each crop in one field. This is because, in those systems, it is assumed that a single plant cultivar, e.g., a product crop for a distribution in the market, is produced in a field, and that all individual plants have practically the same characteristics, rendering no need to distinguish each individual plant. Furthermore, those systems can not identify or manage seeds harvested from each plant. In the systems (1) and (2), the assumed user procedures to be managed are limited to the procedures from the production of the crops to delivery to the consumer. Accordingly, a user procedure management spanning generations of production is not considered in those methods. Similarly, even in the aforementioned method (3), although identification of individual plants can be performed, seeds harvested from each individual plant can not be identified or managed. Therefore, for large scale breeding or genetic research which requires management of seeds harvested from tens of thousands of individual plants, the aforementioned method (3) is not effective.

An object of the present invention is to provide a plant information management system and a plant information management method in which information regarding the seeds of the cultured plants can be readily retrieved, including the parents of the seeds, and the procedures in the production process of the seeds.

SUMMARY OF THE INVENTION

The present invention employs the following in order to achieve the above object.

(1) A plant information management system including: a seed identification information input device which retrieves a value representing a seed to be cultured; an individual plant identification information retrieval device which retrieves a value representing a first individual plant which is produced by germinating the seed; an individual plant identification information input device which retrieves a value representing a second individual plant to be subjected to mating; a new seed identification information retrieval device which retrieves a value representing a new seed obtained by the mating of the second individual plant; a storage location information retrieval device which retrieves information representing a storage location of the new seed; a project database management device which associates the value representing the seed to be cultured, the value representing the second individual plant which is subjected to the mating, the value representing the new seed, and information regarding a process to obtain the new seed, and records the associated information to a project database; a seed database management device which associates the value representing the new seed, the value representing the second individual plant which is subjected to the mating, and information representing the storage location of the new seed, and records the associated information to a seed database; a project database memory device which stores the project database; and a seed database memory device which stores the seed database.

According to the plant information management system, a project database and a seed database are recorded in a project database memory device and seed database memory device, respectively. The information in those two databases are related based on the "value representing the new seed", which is included in both of the two databases. Accordingly, with regard to the seeds of each cultivars, not only the information regarding the parents of the seed, but also the information regarding the process to obtain the seed, can be retrieved readily. Moreover, with regard to a particular seed, even when the operator wishes to know the process to obtain the parents of the seed and further ascendants thereof, the aforementioned effect can be achieved.

In other words, according to the plant information management system, in terms of the seeds of a cultured individual plant, information regarding the parents of the seeds and the process to obtain the seeds can be retrieved readily.

(2) It may be arranged such that: the plant information management system further includes a genetic information input device which accepts an input of genetic information regarding a seed cultivar, wherein the seed database management device records the genetic information which is inputted to the genetic information input device, into the seed database.

In this case, the genetic information of each seed can be readily obtained.

(3) It may be arranged such that, the plant information management system further includes: a field database memory device which stores whether or not each of a plurality of the plats for culturing the seed is in use; and a field database management device which informs to a user whether or not each of the plats is in use, according to a content of the field database memory device.

(4) It may be arranged such that, the plant information management system further includes: a label output device which outputs a label; a label input device which reads the label; and a project management device which instructs the label output device to output the label, in association with a project procedure conducted by the user, wherein: the project database management device stores a content of the label outputted by the project management device and the label output device while relating the content of the label to the project database; and when a label outputted by the label output device in the project procedure is input by the label input device, the project management device instructs the label output device to output a second label of a next project procedure.

(5) It may be arranged such that: in the plant information management system, the project database management device manages information regarding the project to obtain the new seed including a planning date, a transplanting date, a heading date, and a harvest date; and the project database management device outputs the information regarding the project database on a display device in response to input from the user.

(6) It may be arranged such that: the plant information management system further includes an output device which outputs information associated with the seed which is represented by the inputted value by the seed identification information input device, the information being included in the project database and the seed database.

Moreover, the present invention employed the followings in order to achieve the above object.

(7) A plant information management method including the steps of: acquiring a value representing a seed to be cultured; acquiring a value representing a first individual plant produced by germinating the seed; acquiring a value representing a second individual plant to be subjected to mating; acquiring a value representing a new seed obtained by the mating of the second individual plant; acquiring a value representing a storage location of the new seed; associating the value representing the seed to be cultured, the value representing the second individual plant subjected to the mating, the value representing the new seed, and a value regarding a project procedure to obtain the new seed, and recording the associated information as a project database; and associating the value representing the new seed, the value representing the second individual plant subjected to the mating, and the storage location of the new seed, and recording the associated information as a seed database.

(8) It may be arranged such that, the plant information management method further includes the steps of: acquiring genetic information regarding a seed cultivar; and associating the genetic information with information previously inputted to the seed database and recording the genetic information to the seed database.

(9) It may be arranged such that, the plant information management method further includes the steps of: for a plurality of plats to culture the seed, storing whether or not each of the plats is in use; and showing to a user whether or not each of the plats is in use.

(10) It may be arranged such that, the plant information management method further includes the steps of: printing a label associated with a project procedure conducted by a user; associating a content of the label with the information previously recorded to the project database and recording the associated content of the label to the project database; acquiring an input of the label; and when the label associated with the project procedure is inputted, printing a label associated with a next project procedure.

(11) It may be arranged such that, the plant information management method further includes the steps of: recording information regarding the project to obtain the new seed including a planning date, a transplanting date, a heading date, and a harvest date of the project to the project database; and outputting the information in the project database in response to input by a user.

(12) It may be arranged such that: the plant information management method further includes the step of outputting a plurality of pieces of information related to the seed associated with the inputted value by a user, to the project database and the seed database.

BRIEF DESCRIPTION OF THE DRAWINGS

FIG. 2 is a diagram showing the content of a project database.

DETAILED DESCRIPTION OF THE INVENTION

Hereinafter, one embodiment according to the present invention will be described in detail. However, it should be noted that the scope of the present invention is not limited only to the embodiment. In the embodiment, rice is chosen as the model plant. In a production cycle from seeds to next-generation seeds, a series of procedures are conducted, e.g., seed soaking, sowing, transplanting, DNA sampling, mating (including crossing and self-fertilization), harvesting, seed retrieval, and seed storage.

Figure 1:
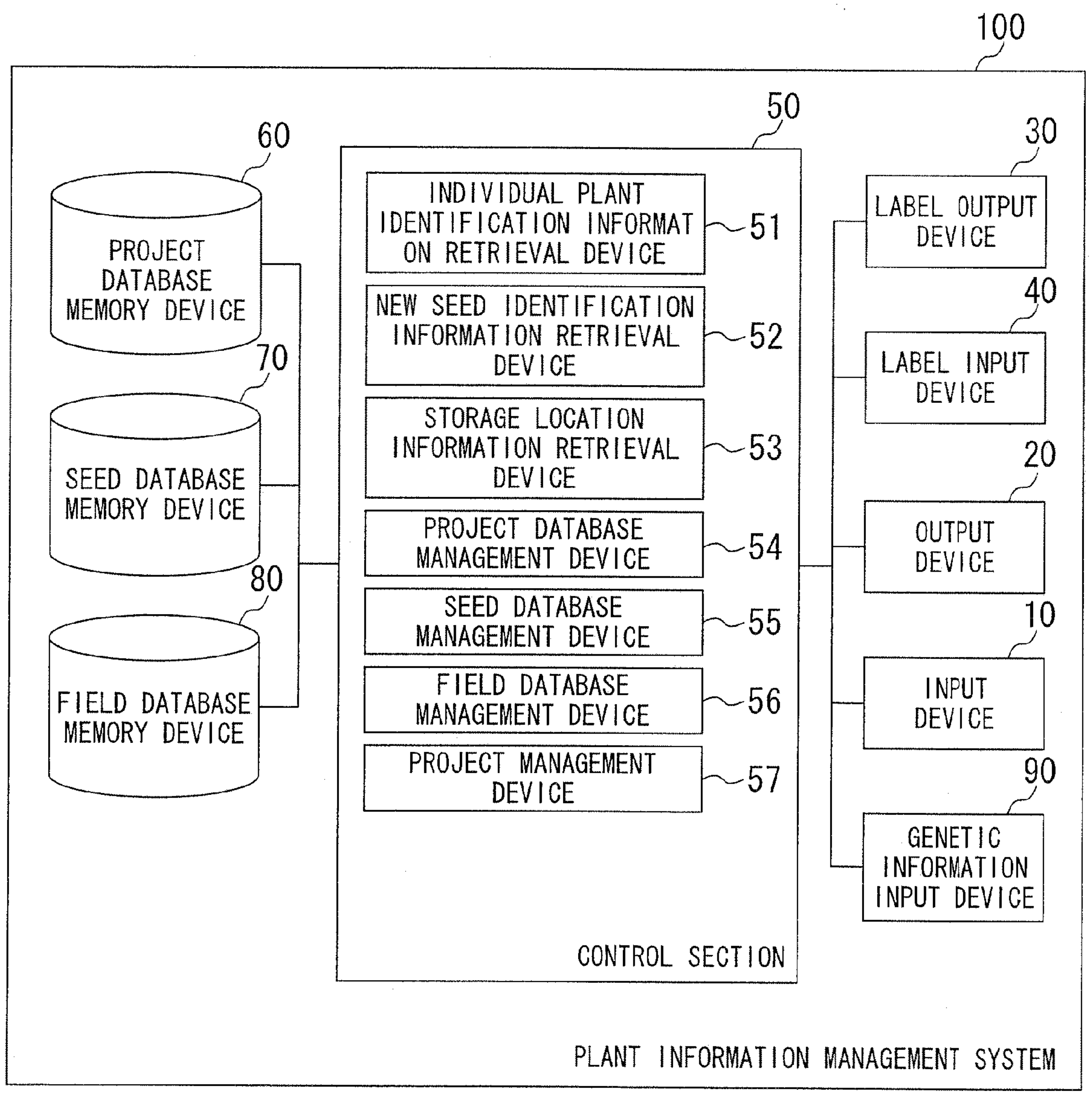
FIG. 1 is a diagram showing functional blocks of a plant information management system according to the present invention.

FIG. 1 is a diagram showing functional blocks of the plant information management system according to the present invention. A plant information management system 100 includes an input device 10, an output device 20, a label output device 30, a label input device 40, a control section 50, a project database memory device 60, a seed database memory device 70, a field database memory device 80, and a genetic information input device 90. The plant information management system 100 may include an information processing device having processors and memory devices connected by a data bus, and operated based on programs stored in the memory device. Each of the functioning devices, or part of which, may be constituted using hardware designed for a particular purpose. Hereinafter, each of the functioning devices included in the plant information management system 100 is explained with reference to FIG. 1.

The input device 10 accepts input from a user, including commands, numerals and text strings. The input device 10 may include, for example, a keyboard, a pointing device (e.g., a mouse, a trackball, a graphic tablet), a dial input device, a touch panel, a numeric keypad, a switch, or a verbal information input device. The input device 10 may be constituted with any device as long as the user of the plant information management system 100 can operate input/selection of commands, numerals, and text strings to the plant information management system 100.

The input device 10, by an operation of the user, accepts information input including project names, names of seeds used in the project (corresponds to the "value representing a seed to be cultured"), amounts of seeds, culture locations used in the project, names of the female parent (seed parent) plant and the male parent (pollen parent) plant used in the mating procedure (corresponds to the "value representing an individual plant to be subjected to mating"), storage locations of the obtained seeds (corresponds to "seed identification information input device" and "individual plant identification information input device"). In the embodiment, names of seeds, individual plants, locations, and the like are not limited to literal names. Identifiers including, for example, a series of characters and/or numerals can also be used, as long as each of the seeds, the individual plants, or the locations can be identified thereby.

The output device 20 includes a device which displays images and letters on a screen. For example, the output device 20 may be constituted using a cathode ray tube (CRT) display, a liquid crystal display, or an organic electro-luminescent (EL) display, or the like. Moreover, the output device 20 includes a device which prints images and letters on a sheet. For example, the output device 20 may include an ink-jet printer, or a laser printer. The output device 20 may also include a device which outputs letters by converting them into audio signals. In the above case, the output device 20 may include a voice synthesizer and a sound output device (e.g., a speaker). The output device 20 displays the content of the project database, in accordance with the information of a project database management device 54. The output device 20 displays the content of a seed database management device 55 and a field database 56, following the information from a seed database 55 and the field database 56. The output device 20 displays the content of the databases while relating the content to each other, according to the information from a project management device 57 or the database management devices (54 to 56). For example, if information (e.g., name of a seed or a name of a field) is inputted by the input device 10, the project database management device 54, the seed database 55, and the field database 56 may output information stored therein which is related to the inputted information, e.g., the name of the seed, the name of the individual plant related to the field, the planning date of the project which produced the individual plant, the transplanting date of the individual plant, the harvesting date, the heading date, or the genetic information of the individual plant. The field database 56 may display such information on the output device 20. Management of databases as explained above can be realized by using previously known technologies of the relational database.

The label output device 30 includes a device which prints a label on a sheet. The label output device 30 generates a barcode including text and figure information outputted from the control section 50 (project management device 57). The label output device 30 prints the generated barcode and the text and images as directed by the control section 50, onto the sheet provided in the label output device 30, thereby outputting a label.

The label input device 40 includes a device which reads the label printed by the label output device 30, which consists of barcodes, text, and images. The label input device 40 decodes the inputted barcode, thereby retrieving text and figure information. The label input device 40 (corresponds to "individual plant identification information input device") is operated by the user to input the names of the female parent individual plant and the male parent individual plant (corresponds to the "value representing an individual plant to be subjected to mating").

The device may be constituted so that the names of the female parent individual plant and the male parent individual plant can be inputted by either of the input device 10 and the label input device 40. On the other hand, in the mating procedure (described in detail later), when the control section 50 (project management device 57) tries to confirm whether or not the individual plant used in the mating process is appropriate, the user can use only the label input device 40 for this purpose. As described in detail later, this constitution prevents erroneously mating wrong individual plants.

The control section 50 performs a control operation of the output device 20 and the label output device 30, and also performs read/write control into/from the memory devices (60 to 80) of each of the databases, based on the information inputted from the input device 10 and the label input device 40.

The control section 50 includes an individual plant identification information retrieval device 51, a new seed identification information retrieval device 52, a storage location information retrieval device 53, a project database management device 54, a seed database management device 55, a field database management device 56, and a project management device 57. The devices included in the control section 50 may be realized by running programs on a CPU, or by using a group of specialized hardware. Specific operations of each of the devices included in the control section 50 will be described later.

Each of the project database memory device 60, the seed database memory device 70, and the field database memory device 80 includes a nonvolatile memory device, e.g., a magnetic had disk drive, or a semiconductor memory device, in order to store the content of the databases. The content of each of the databases will be explained below.

FIG. 2 shows the content of the project database. The project database includes information regarding projects to be performed by the user.

The project database includes a project name, information regarding the used seeds, information regarding the individual plants obtained from the seeds, information regarding the mating, and the progress status of each procedure. As the progress status of each procedure, the project database may include the planning date of the project, the transplanting date in the transplanting procedure, the heading date, and the harvest date.

The project name is identifier information regarding the project. By using the project name, the user can identify a particular project from among the projects stored in the project database. The information regarding the seeds to be used includes, for each seed cultivar to be used, the name of the seed, the amount of the seeds to be used, the information regarding the location to be used for the culture of the seeds. The information regarding the individual plants obtained from the seeds includes, for each individual plant obtained from the seeds, a name issued to represent the individual plant, and the information regarding the culture location of the individual plant. The information regarding the mating includes, for each mating performed in the mating procedure, the name of the female parent plant, the name of the male parent plant, the name issued to represent the offspring obtained by the mating. The progress status of procedure includes, for each of the procedures, information whether or not the procedure has been performed.

Figure 3:
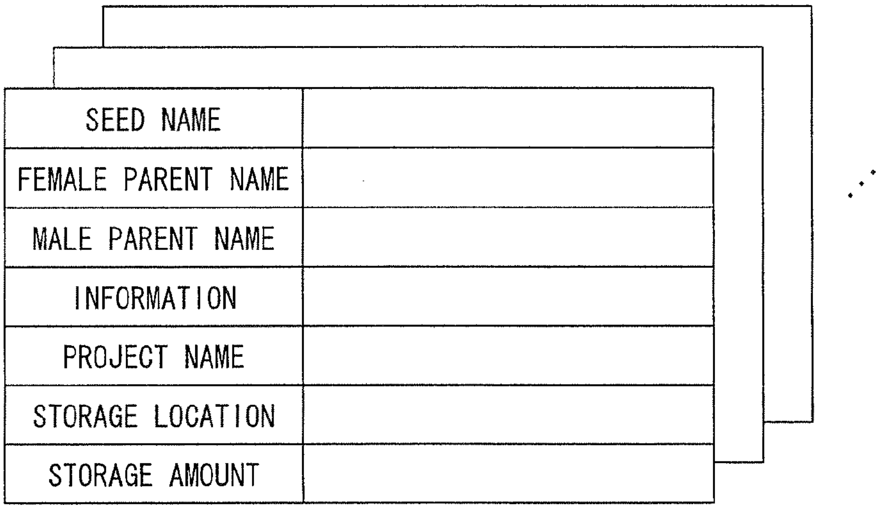
FIG. 3 is a diagram showing the content of a seed database.

FIG. 3 shows the content of the seed database. The seed database includes information regarding the seeds of each cultivar. For each seed cultivar, the seed database includes, the name of the seed, the name of the parent individual plants (the female and male parent), the genetic information, the name of the project which produced the seeds, the information regarding the storage location, the remaining amount of the seeds. The information regarding the storage location is information specifying the storage location, e.g., the location of the storage shelf, and the section in the shelf storing the seeds. For the genetic information, the genetic information itself may be included in the seed database. Alternatively, an link to a data file containing the genetic information, or a storage location thereof may be used.

Figure 4:
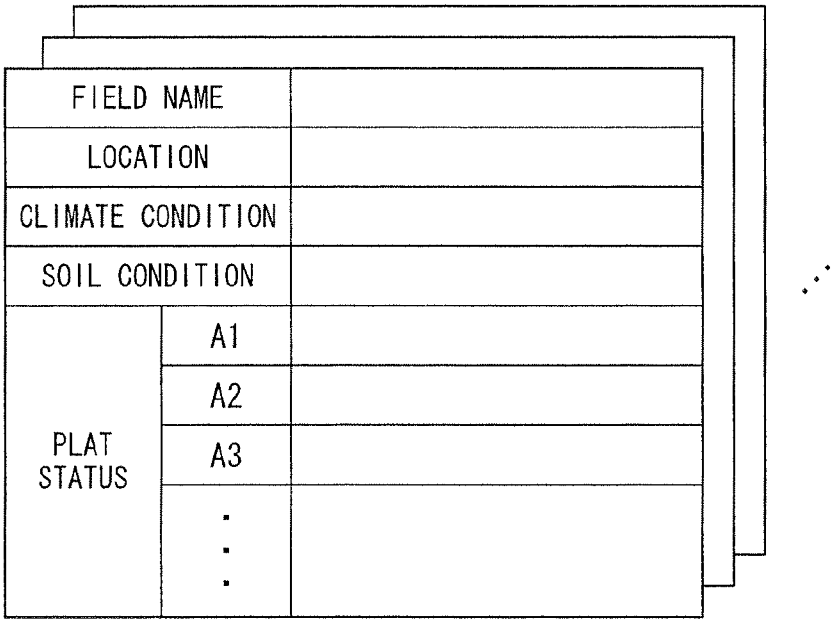
FIG. 4 is a diagram showing the content of a field database.

FIG. 4 shows the content of the field database. The field database includes the name of the field, the location of the field, the climate condition, the soil condition, the status of each plat included in the field. The status of each plat in the field shows whether or not the plat is currently in use, e.g., whether or not any project is using the plat. The configuration of the plats within a field is arbitral and not limited to any particular configuration, as long as each plat has the necessary space to culture one individual plant. However, it is preferable to divide and name the plats so that each plat corresponds to each well of 96-well, or 384-well plate, which are used commonly in the field of molecular biology and biochemistry. This way, in the analysis procedure (described later), such as DNA analysis, identification of the samples can be performed in an organized manner. For example, a field may be divided into 8 rows (A to H) and 12 columns (1 to 12). The plat of first column in the row A is named A1, and the plat of twelfth column in the row H is named H12. When the field has sufficient space, it is preferable to divide the field into plats corresponding to a plurality of 96-well plates.

The genetic information input device 90 inputs genetic information analyzed by other devices, into the plant information management system 100. The genetic information input device 90 may adapt any technical constitution, as long as it can transfer or input genetic information data from other devices. For example, when the genetic information is recorded on a memory device such as a compact disc (CD), a digital video disc (DVD), a magneto-optical drive disc (MO), or a semiconductor memory device, the genetic information input device 90 can be constituted using a reader device for those memory devices. Alternatively, the genetic information input device 90 may include a network device which can communicate with other devices through networks, e.g., internet, short range wireless communication, or a universal serial bus (USB), so that genetic information can be acquired from other devices. Moreover, when a functional device which analyzes genetic information is included in the plant information management system 100, the genetic information input device 90 may acquire the genetic information from the functional device.

Hereinafter, the operation processes will be explained, for running a project in order to obtain new cultivar seeds, using the plant information management system 100. The project includes, as explained earlier, the planning procedure, the seed soaking procedure, the sowing procedure, the transplanting procedure, the mating procedure, the harvest procedure, the seed retrieval procedure, and the storage procedure.

Figure 5:
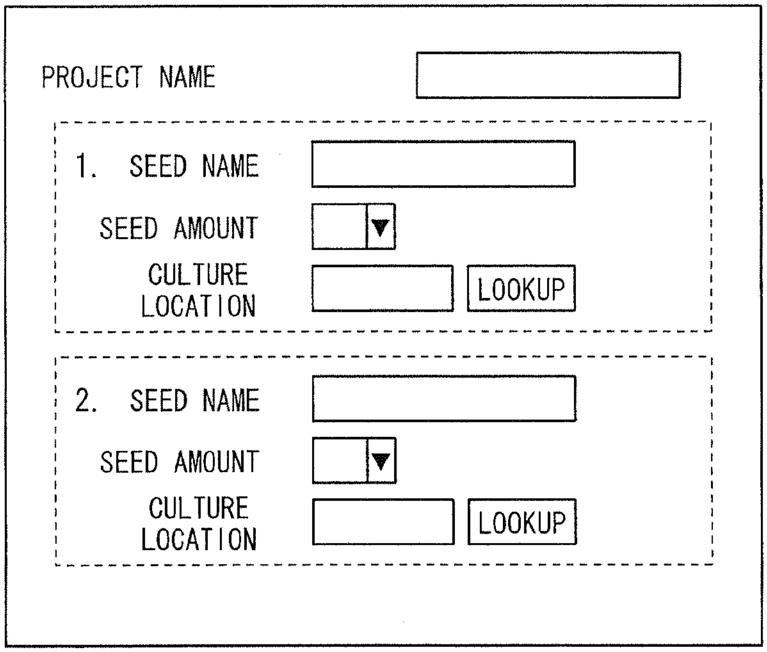
FIG. 5 is a diagram showing an example of a planning input screen.

When performing a planning procedure of the project, the user operates the input device 10 and directs the plant information management system 100 to perform a planning procedure. The project management device 57, in response to this operation, instructs the output device 20 to display a planning input screen. FIG. 5 shows an example of a planning input screen. The planning input screen includes input boxes for inputting the project name, the name of seeds to be used, the amount of seeds to be used, the culture location of each seed (field name and plat name). The user inputs required information into each input box, by operating the input device 10.

On the planning input screen, the user can input the culture location by using a plat map. In the planning input screen, when the "lookup" key is selected by the user, the field database management device 56 responds by instructing the output device 20 to display the field name list. In the field name list, the names of available fields will be listed. When the user selects one field from the field name list, the field database management device 56 responds by reading data regarding the corresponding field. Thereafter, by the command of the field database management device 56, the output device 20 displays the plat map of the selected field.

Figure 6:
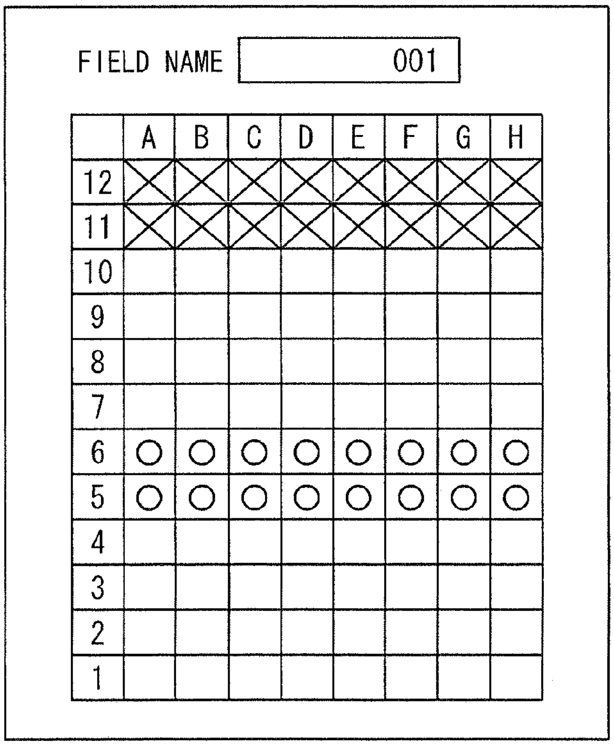
FIG. 6 is a diagram showing an example a screen of field plat map.

FIG. 6 shows an example of the screen of a field plat map. The field database management device 56 determines the content of the plat map, by reading the content of the field database which is related to the corresponding field. The plat map shows the status of the 96 plats from A1 to H12. The status of a plat can either be "available", "used by other project", or "reserved". When a plat is used or reserved, a cross is displayed on the plat. This display is determined by the field database management device 56, according to the content of the plat status in the field database.

The user operates the input device 10 and select a plat to be used in the project, from among available plats. A circle is displayed on the selected plat. When the user determines the selection, the plat status of the selected plat becomes "used", and the field database is updated by the field database management device 56 accordingly.

The plat map may also display information including the name of the individual plant cultured in the plat, the project name using the plat, the reservation period for the project. The user can determine plats to be used for transplantation, as many as the number of individual plants to be transplanted, considering the information displayed on the plat map.

After completing the input of required information on the planning input screen, the seed database management device 55 retrieves the remaining amount of the seeds which is inputted as the seed to be used, from the seed database. The project management device 57 compares the inputted amount of the seeds to be used with the retrieved remaining amount of the seeds. If the remaining amount is larger than the inputted amount, the seed database management device 55 determines that the project can be operated. After the determination, the project database management device 54 writes the inputted information onto the project database. On the other hand, if the remaining amount is smaller than the inputted amount, the project management device 57 outputs an error massage on the output device 20, informing that the project can not be operated, prompting the user to reconsider the planning.

Figure 7:
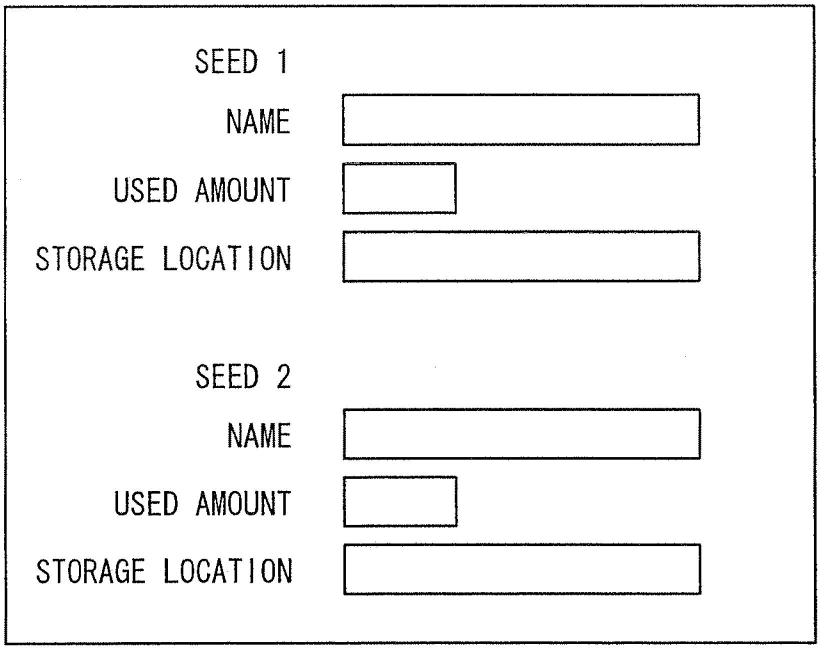
FIG. 7 is a diagram showing an example a screen of used seed information.

When the inputted project is operable, the project management device 57 commands the output device 20 to display the used seed information screen. FIG. 7 is an example of the used seed information screen. In the used seed information screen, information inputted at the planning input screen is displayed, e.g., the seed name corresponding to the seed to be used, the amount of the seeds to be used, the storage location. The storage location information can be displayed on the output device 20, by the seed database management device 55 retrieving the storage location information related to the seed, from the seed database. When the input process of the planning input screen is finished, the used seed information screen shows the user information including the storage location and the amount of the seeds to be used in the project.

Figure 8:
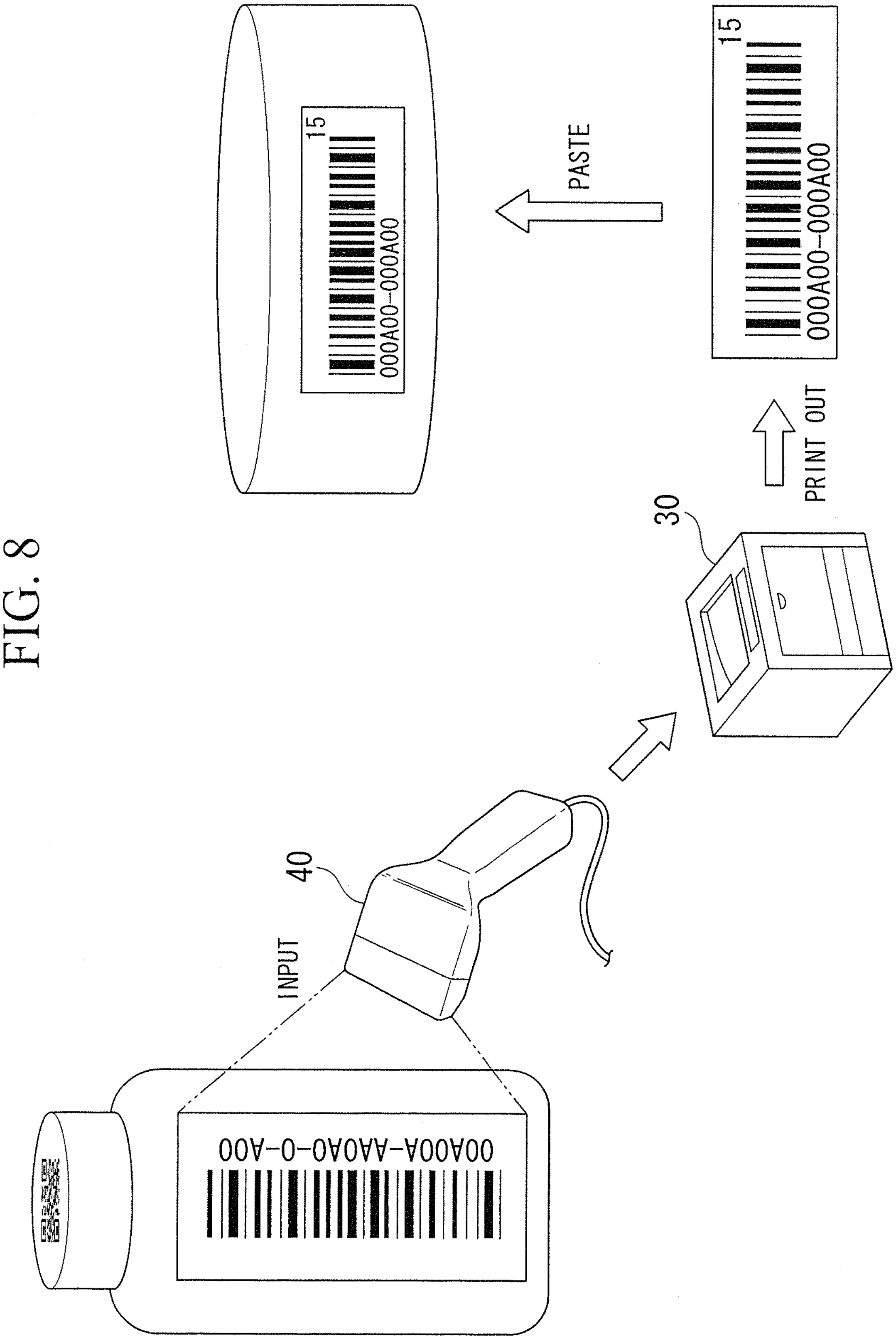
FIG. 8 is a diagram showing part of the user operations in the seed soaking procedure.

After finishing the planning procedure, the user performs the seed soaking procedure. FIG. 8 shows part of the user operations in the seed soaking procedure. In the seed soaking procedure, the user operates, the input device 10 to specify the project. Thereby, the user notifies the plant information management system 100 that a seed soaking is being operated. The project management device 57, in response to this input, prompts the user to read the label of the seed to be used in the project, through the display of the output device 20. In response, the user reads the labels of each of the seeds to be used in the project, using the label input device 40. The labels of the seeds are attached to the shelf in which the seeds are stored, or to the bottle in which the seeds are stored. The label may contain the name of the seeds.

When a label is read, the project management device 57 decides whether or not the seed related to the label matches any of the seeds to be used in the present project. If there is no match, the project management device 57 outputs the result on the output device 20, together with the names of the seeds to be used in the project and the storage location thereof. Then, the project management device 57 prompts the user to re-read the label of the appropriate seed using the label input device 40. Then, the project management device 57 waits for the input of the appropriate label.

On the other hand, when the seed related to the read label is determined to match any of the seeds to be used in the present project, the project management device 57 notifies the result to the seed database management device 55. Then, the seed database management device 55 updates the amount of the seeds stored in the seed database, by subtracting the amount to be used. The project management device 57 commands the label output device 30 to print a label for the seed soaking of the seed (seed soaking label). The seed soaking label includes, for example, the project name, the seed name, and the seed amount. The project database management device 54 records that the seed soaking procedure of the project is performed, onto the project database.

According to the command from the project management device 57, the label output device 30 prints the seed soaking label for the seeds (the "Print out" process shown in FIG. 8). The user pastes the seed soaking label onto a container for soaking, e.g., a Petri dish (the "Paste" process shown in FIG. 8). The user stacks a piece of wet cotton wool in the container, and puts the seed thereon, in order to germinate the seed.

In practice, the seed soaking for a group of seeds with the same name is performed in a single seed soaking container. In this case, the seed soaking label may include the text information regarding all the planned culture locations for each of the seeds included in the same seed soaking container. By indicating the planned culture location on the seed soaking label, in the transplanting process for the germinated individual plants, the transplanting can be performed securely by following the printed locations on the seed soaking label. Therefore, there is an advantageous effect of reducing mistakes in culture location. For example, when ten seeds of the same kind are being soaked, if the planned culture locations for those seeds are plats A1 to A10 in the field X1, then the seed soaking label may include a description "X1A1 to X1A10".

Figure 9:
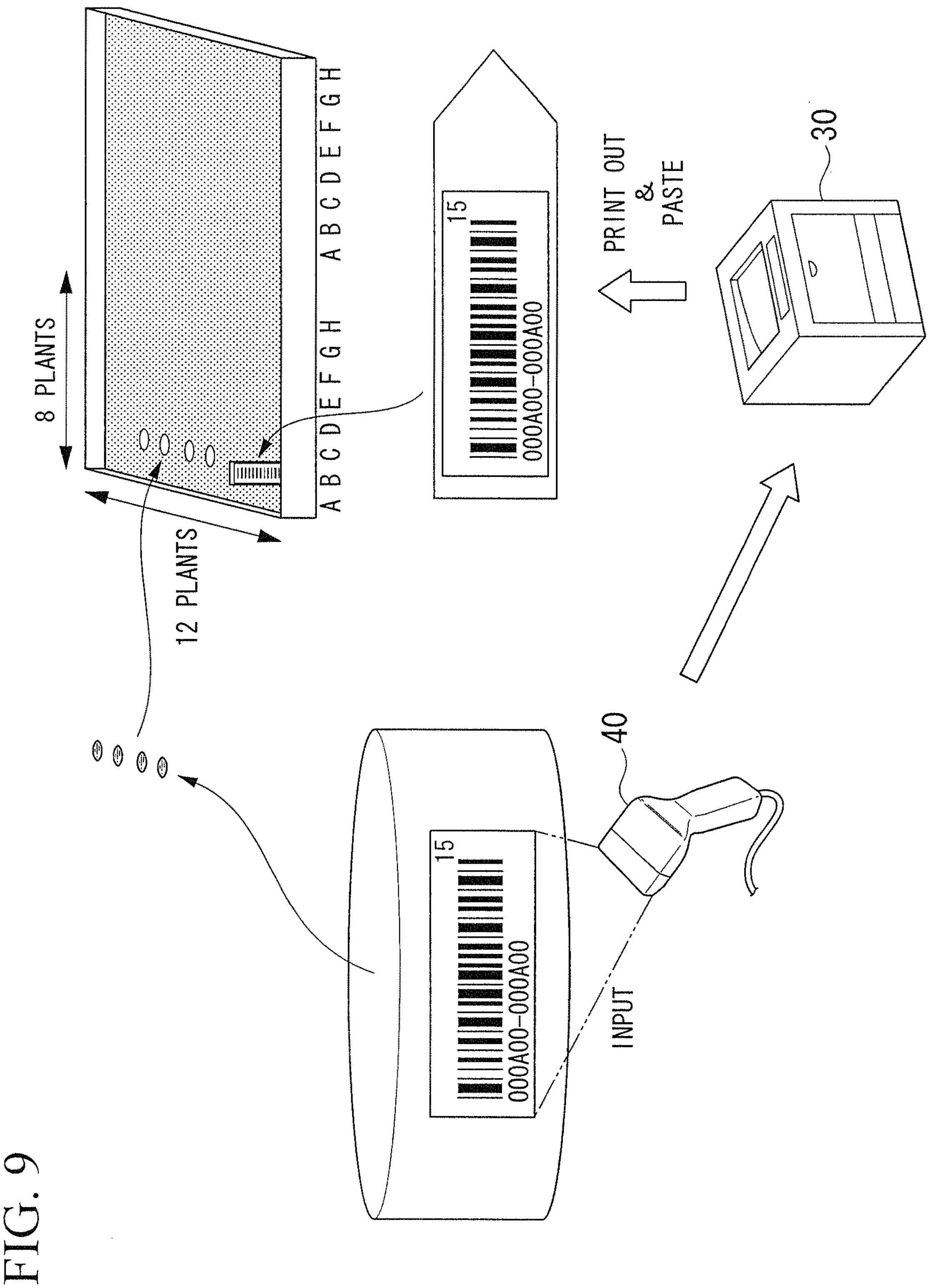
FIG. 9 is a diagram showing part of the user operations in the sowing procedure.

After the seed soaking, the user performs the sowing procedure. FIG. 9 shows part of the user operations in the sowing procedure. In the sowing procedure, the user operates the input device 10, in order to specify the project. Thereby, the user notifies the plant information management system 100 that a seed soaking is being operated. The project management device 57, in response to this input, prompts the user to read the seed soaking container label used in the project, through the display of the output device 20.

In response, the user reads the seed soaking container label, using the label input device 40 (the "Input" process shown in FIG. 9). The project management device 57 decides whether or not the content of the label (e.g., the seed name) matches the content recorded in the project database related to the specified project. If there is no match, the project management device 57 outputs the result on the output device 20, pausing further processes including individual plant name issuance, or recording thereof. Then, the project management device 57 waits for an input of the appropriate label. On the other hand, if the read label content matches the database record, the project management device 57 prompts the user to input the number of the individual plants to be sown, on the output device 20. In response, the user inputs the number of the individual plants to be sown, using the input device 10. In response to this input, the individual plant identification information retrieval device 51 generates identifier names for each of the individual plants soaked in this project, according to the inputted number. Alternatively, the individual plant identification information retrieval device 51 may retrieve the individual plant name from the user, by prompting the user to input names using the input device 10.

The project management device 57 assigns culture locations for each individual plant, according to the inputted number. The culture locations previously selected by the user in the planning procedure are used. The project database management device 54 records the issued names and corresponding culture locations, onto the project database.

The project management device 57 commands the label output device 30 to print sowing labels each containing the individual plant name and the culture location, as many as the inputted number. The label output device 30, in response, prints sowing labels (the "Print out" process as shown in FIG. 9). The sowing labels may be printed separately for each individual plant, or for each row or column of the plats. The project database management device 54 records that the sowing procedure is performed in the project, onto the project database.

The user performs sowing, for each of the individual plant, into a plug-tray (raising tray) corresponding to the assigned culture location, according to each of the printed label. The user pastes a sowing label on a post or a plate (the "Paste" process shown in FIG. 9). The user may put the post or plate on the soil next to the individual plant. Alternatively, the sowing label may be directly pasted on the raising tray.

The raising tray is also partitioned in the similar manner as the field, so that one plat thereof has sufficient space for one individual plant to be cultured. Moreover, the configuration of the raising tray plats is provided so as to correspond to the configuration of the field plats. For example, when the field is divided into 8 rows (A to H) and 12 columns (1 to 12), the raising tray is also partitioned into 8 rows (A to H) and 12 columns (1 to 12). By using corresponding plat configurations for the raising tray and the field, each of the plats printed on the sowing label can be corresponded to a plat in the field. Therefore, in the transplanting procedure from the raising tray to the field, transplanting can be efficiently performed from a plat to a corresponding plat. Therefore mistakes in transplantation procedure can be avoided.

For example, when ten individual plants are being transplanted, and the seed soaking label attached on the seed soaking container has a description "X1A1 to X1A10" as the reserved culture plats, one 96-patitioned region in the raising tray is labeled as X1, and into each of A1 to A10 plats is the X1 region, one germinated individual plant is sown. Thereafter, after the individual plant is sufficiently grown, the individual plant raised in the A1 plat of X1 region on the raising tray is transplanted to the A1 plat of the X1 field, and the individual plant raised in the A2 plat of X1 region on the raising tray is transplanted to the A2 plat of the X1 field. By the above described systematic transplantation method, cultivar mistaking in the transplanting procedure can be reduced. Transplanting procedure will be described in detail later.

In a case where only 8 seeds out of 10 seeds are being sown, A1 to A8 plats of the raising tray is used for sowing one individual plant each, but A9 and A10 plats are not used. Moreover, in the transplanting procedure from the raising tray to the field, if the individual plant of the A5 plat dies, then only seven individual plants in the A1 to A4 and A6 to A8 plats are transplanted into each corresponding plats of the field, but A5 plat is not used. In this way, when some seeds have not germinated in the sowing procedure, or some individual plants died for any reason during the growth, the culture plats reserved for the dead plants are not used. In this method, each of the individual plant names and the culture locations match each other without confusion, resulting in a reduction of mistakes in the procedures.

Figure 10:
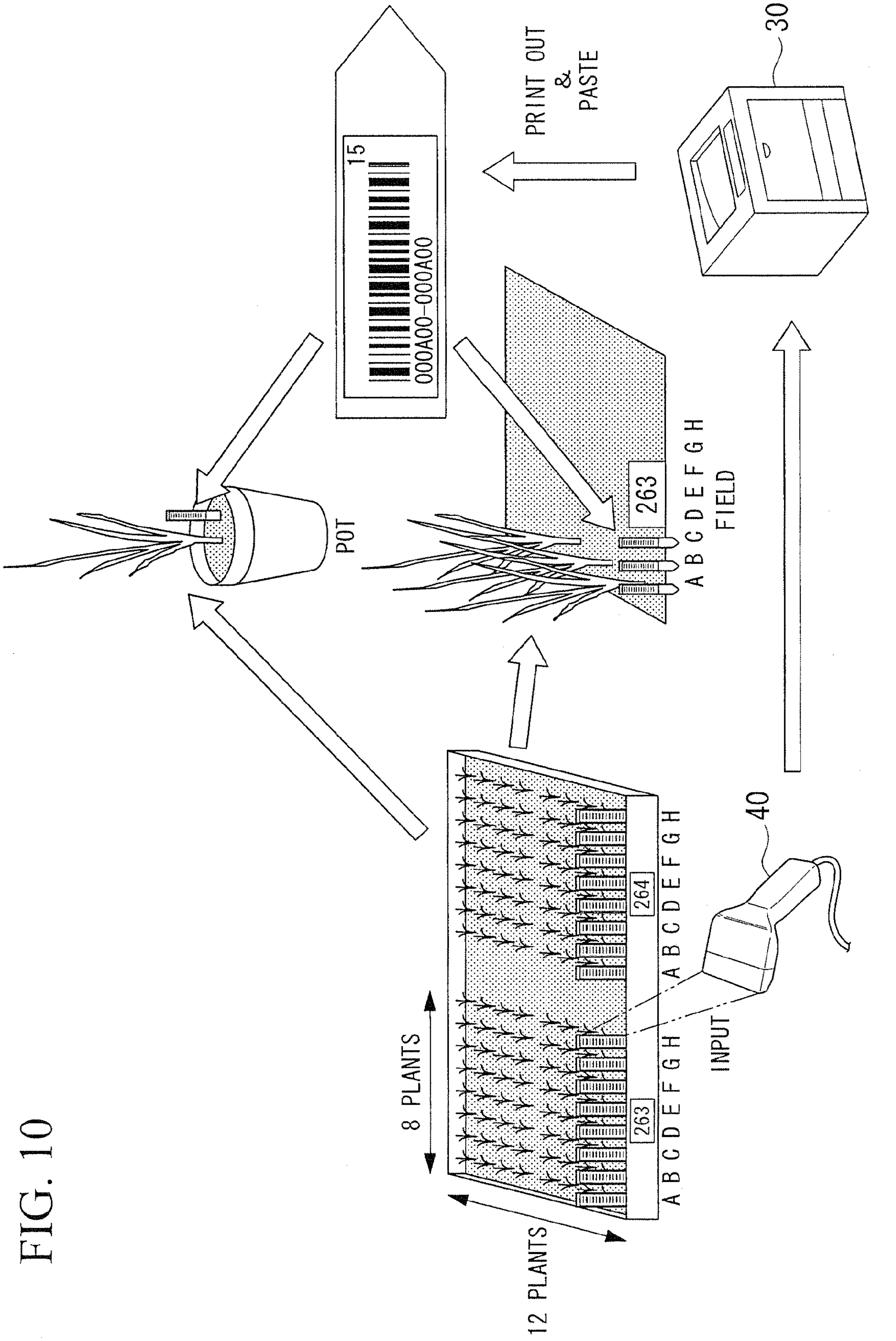
FIG. 10 is a diagram showing part of the user operations in the transplanting procedure.

After the sowing and the germination, the user performs the transplanting procedure. FIG. 10 shows part of the user processes in the transplanting procedure. In the transplanting procedure, the user specifies the project, by operating the input device 10. Thereby, the user notifies the plant information management system 100 that a transplanting is being operated. The project management device 57, in response to this input, prompts the user to read the label on the plug-tray used in the project, through the display of the output device 20.

In response, the user reads the label on the plug-tray, using the label input device 40 (the "Input" process shown in FIG. 10). The project management device 57 decides whether or not the content of the label (e.g., the seed name) matches the content recorded in the project database related to the specified project. If there is no match, the project management device 57 outputs an error output, pausing further processes including individual plant name issuance, or recording thereof. Then, the project management device 57 waits for an input of the appropriate label. On the other hand, if the read label content match the database record, the project management device 57 prompts the user to input the number of the germinated individual plants, on the output device 20. In response, the user inputs the number of the germinated individual plants, using the input device 10.

The project management device 57 commands the label output device 30 to print transplanting labels each containing the individual plant name and the culture location, as many as the inputted number. The label output device 30, in response, prints transplanting labels (the "Print out" process as shown in FIG. 10). The transplanting labels may be printed separately for each individual plant, or for each row or column of the plats. The project database management device 54 records that the transplanting procedure is performed in the project, onto the project database.

The user transplants each of the individual plants to the field corresponding to the culture location printed on the label. The user pastes a transplanting label on a post or a plate (the "Paste" process shown in FIG. 10). The user puts the post or plate on the soil next to the individual plant.

In the sowing and transplanting procedures, the user may sow the soaked seeds (individual plants) to a raising tray, e.g. a plug-tray. After a certain period of growth, the individual plants may be transplanted to the field. Alternatively, the soaked seeds can be directly sown to the field. Moreover, in the transplanting procedure, the user may perform transplanting on a field (the "Field" as shown in FIG. 10). Alternatively, each individual plant may be transplanted to an individual pot (the "Pot" as shown in FIG. 10).

Figure 11:
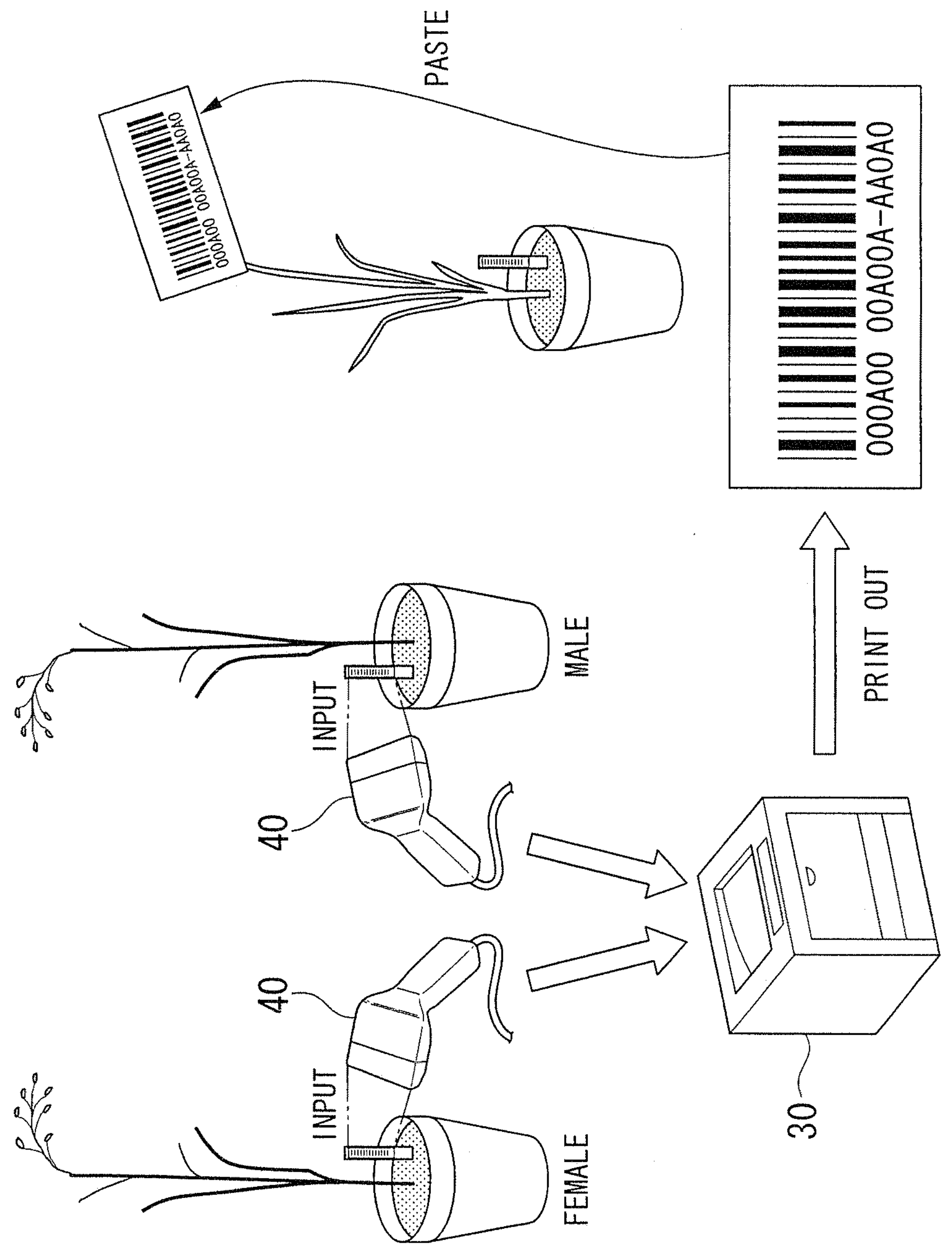
FIG. 11 is a diagram showing part of the user operations in the mating procedure.

After transplanting, when the individual plants are grown to a mature stage wherein mating is possible, the user performs the mating procedure. FIG. 11 shows part of the user processes in the mating procedure. The user mates selected individual plants, to obtain new generation individual plants, and thereby produce a new cultivar. In the mating procedure, the user specifies the project, by operating the input device 10. Thereby, the user notifies the plant information management system 100 that a mating is being operated in the project. The project management device 57, in response to this input, prompts the user, through the display of the output device 20, to read the labels of a female individual plant and a male individual plant using the label input device 40.

In response to the prompt, the user selects individual plants to be used in the mating. The user reads the labels of the female individual plant and the male individual plant, using the label input device 40 (the "Input" process as shown in FIG. 11). The project management device 57, according to the content of the inputted label, decides whether or not the individual plants selected for the mating are correct, that is, whether or not the individual plants are grown in the particular project. When the selections are correct, the project database management device 54 records the information regarding the inputted labels to the project database as the mating parents data. Moreover, the new seed identification information retrieval device 52 issues a new seed name. Then, the project database management device 54 and the seed database management device 55 relate the new seed name to the parent individual plant names, and record the information to the project database and the seed database, respectively. Alternatively, the new seed identification information retrieval device 52 may retrieve the new seed name, by prompting the user to input a new seed name, operating the input device 10.

Thereafter, the project management device 57 commands the label output device 30 to print a mating label including parent individual plant names. Accordingly, the printed mating label includes two names: the name of the female parent individual plant; and the name of the male parent individual plant. The label output device 30 prints mating labels, according to the instructions of the project management device 57 (the "Print out" process as shown in FIG. 11). Thereafter, the project management device 57 records that the mating is performed in the project, onto the project database. The printed mating label may further include the information regarding mating date, the operator of the mating operation, or the like.

The user retrieves the mating labels outputted from the label output device 30, and pastes them onto bags (the "Paste" process as shown in FIG. 11). The user also performs mating, using the female individual plant and the male individual plant. The mating may be performed using the standard procedures. For example, the pollen obtained from the male parent is pollinated on the pistil of the female parent. Thereafter, the pistil is covered by a bag or the like, in order to prevent the effects from other pollen. At this time, the user uses the above explained labeled bag, to cover the pistil.

On the other hand, if the selections are not appropriate, the project management device 57 informs, on the output device 20, that the individual plants cultured in the present project should be selected. At this time, the project management device 57 may display, on the output device 20, the culture locations used in the present project. Thereafter, the project management device 57 prompts, through the display of the output device 20, the user to re-read the labels of the correct individual plants, using the label input device 40. Then, the project management device 57 waits for the inputs of the appropriate labels.

Figure 12:
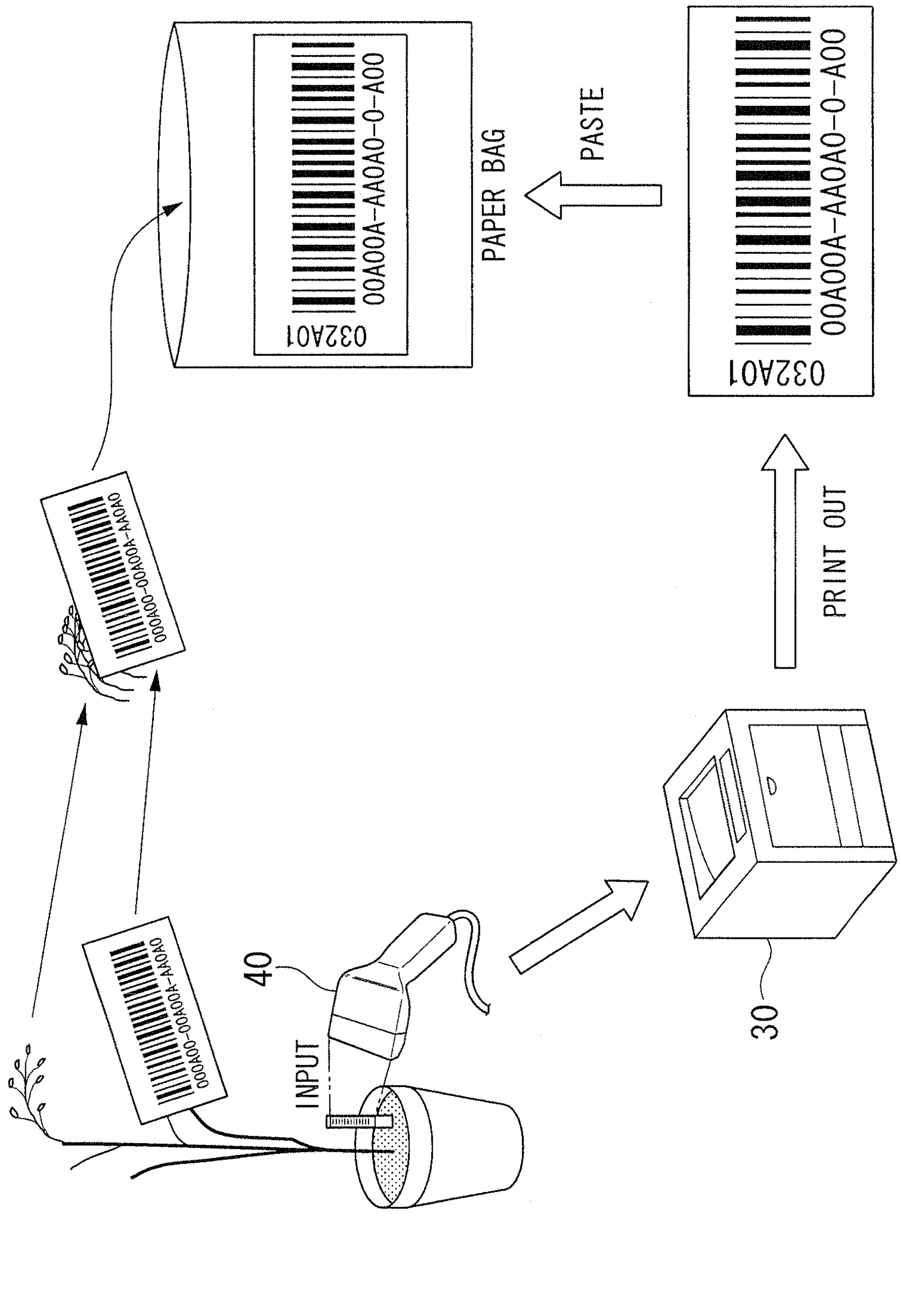
FIG. 12 is a diagram showing part of the user operations in the harvesting procedure.

When the mated female individual plant produces seeds, the user performs the harvest procedure. FIG. 12 shows part of the user processes in the harvest procedure. In the harvest procedure, the user operates the input device 10 to specify the project. Thereby, the user inputs to the plant information management system 100 that the harvest is being operated. The user selects the female individual plant to be harvested. The project management device 57, in response to the input, commands the output device 20 to output a display prompting the user to read the label of the female individual plant to be harvested. In response, the user selects the female individual plant to be harvested, and reads the label of the bag covering the head, using the label input device 40 (the "Input" process as shown in FIG. 12). At this time, the use may read only the name of the female individual plant. Alternatively, the user may read the names of the female individual plant and the male individual plant.

The project management device 57 decides whether or not the content of the inputted label are related to the present project. If the content of the inputted labels are of the present project, the project database management device 54 retrieves the name of the seed recorded in the project database which is related to the name of the female individual plant (or, the names of the female and male individual plants). Thereafter, the project management device 57 prints a harvest label including the seed name, by using the label output device 30. The harvest label includes, for the seeds produced by self-pollination, the seed name, the information regarding the female parent individual plant, and the fact that the seed is obtained by self-pollination. On the other hand, for the seeds produced by mating, seed name, mating information, e.g., mating name, and the individual plant information regarding the female parent and the male parent, is included. The label output device 30 prints harvest labels, according to the command of the project management device 57 (the "Print out" process as shown in FIG. 12).

The user retrieves the harvest labels printed from the label output device 30, and pastes them on the harvest bags (the "Paste" process as shown in FIG. 12). The user harvests the head from the intended individual plant, and stores the head into the harvest bag. The user reads the content of the label attached to the harvest bag, using the label input device 40. The project management device 57 records that the harvest of the individual plant related to the inputted name is finished, on the project database.

When the content of the inputted label is related to a different project, the project management device 57 commands the output device 20 to output the fact that the label of an individual plant related to the different project is inputted, and also output the name of the individual plant related to the present project, and the culture location thereof. The project management device 57 prompts, through the display of the output device 20, the user to re-read the label of the correct individual plant, using the label input device 40. Thereafter, project management device 57 waits for the input of the appropriate labels.

The harvest label may include character information regarding the seed name, the culture location name of the individual plant to harvest the seed. Since the label attached to the harvest bag includes the location information regarding the individual plant to be harvested, the user can precisely retrieve the plant tissue including the seeds from the target individual plant. The harvested plant tissue can be subjected to standard procedures including drying, while enclosed in the harvest bag.

Figure 13:
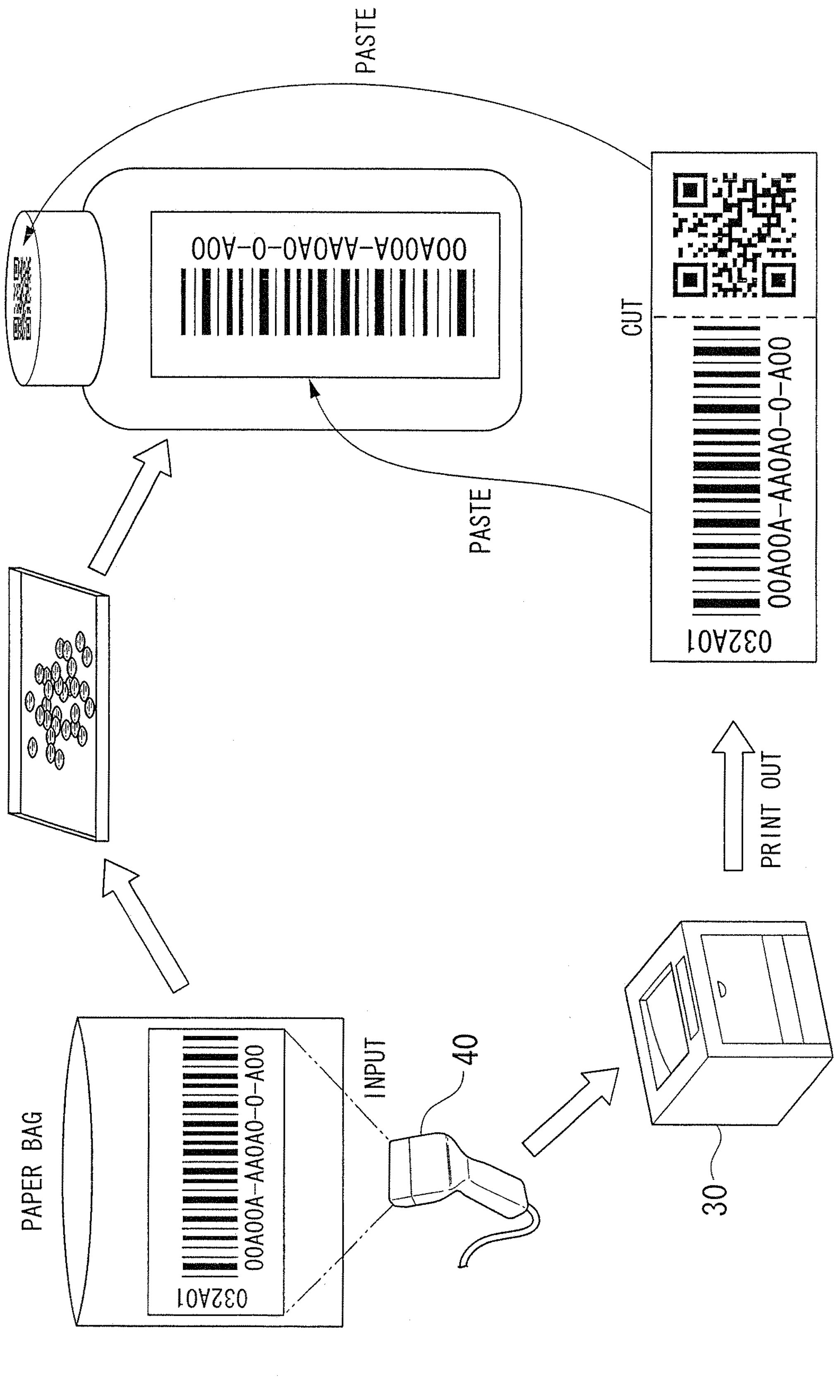
FIG. 13 is a diagram showing part of the user operations in the retrieval and storage procedure.

After the harvest is finished, the user performs procedures of retrieval and storage. FIG. 13 shows part of the user processes in the retrieval and storage procedures. In this procedure, the user operates the input device 10 and specifies the project. Thereafter, the user inputs to the plant information management system 10 that the seed retrieval and storage are being performed in the project. In response, the project management device 57 commands the output device 20 to display a screen to prompts the user to read the label, using the label input device 40, of the harvest bag which includes the head of the seeds to be retrieved and stored.

In response to the prompt, the user reads the label attached to the harvest bag which includes the head of the seeds to be retrieved, using the label input device 40 (the "Input" process as shown in FIG. 13). The project management device 57, when the content of a label is read, decides whether or not the content of the label are related to the present project. If the content of the label are related to the present project, the storage location information retrieval device 53, according to the inputted label, assigns a new storage location for the seeds, and retrieves information related to the new storage location. The seed database management device 55 relates the information regarding the storage location, which is retrieved by the storage location information retrieval device 53, to the retrieved seeds, and records the information into the seed database. The project management device 57 commands the label output device 30 to print a storage label for the seed. The label output device 30, according to the command of the project management device 57, prints the storage label (the "Print out" process as shown in FIG. 13).

The storage label includes information regarding the seed name, the storage location and the like. The project management device 57 commands the output device 20 to display the new storage location. The storage location, instead of assigned by the storage location information retrieval device 53, may be arbitrarily decided and inputted by the user. In this case, the storage location information retrieval device 53 retrieves the information regarding the storage location from the user.

After reading the label, the user takes out the head from the harvest bag, and performs an operation of threshing or the like. Thereby, the user retrieves the seeds from the head. The user stores the retrieved seeds into a bottle. The user then pastes the storage label printed by the label output device 30 onto the bottle (the "Paste" process as shown in FIG. 13). The user inputs the amount of the seeds into the plant information management system 100 using the input device 10, as the remaining seeds amount. In response to this input, the seed database management device 55 records the remaining seeds amount onto the seed database. Thereafter, the user stores the bottle with an attached storage label, at a storage location assigned by the plant information management system 100. The label output device 30 may print a plurality of storage labels. In this case, for example, one label may be printed in a form which can be pasted on a bottle cap, having information format within a smaller area (e.g., two-dimensional bar code). The other label may be printed in a format in which the information is printed in a visibly readable manner (e.g., numbers and alphabets).

When the inputted label content are related to a different project, the project management device 57 commands the output device 20 to output the fact that the harvest label related to a wrong project has been inputted, and also the name of the individual plant related to the present project, and the culture location thereof. The project management device 57, through the display of the output device 20, prompts the user to re-read the appropriate harvest label, using the label input device 40. The project management device 57 waits for the input of the appropriate labels.

The user can perform a genetic information analysis, any time after the transplanting of the plant to the field, before the individual plant dies, by sampling the plant tissue, e.g., leaves thereof, and extracting DNA from the tissue. In view of the advancing technology in the recent years in the fields of recombinant DNA and the like, retrieving genetic information regarding each individual plant and analyzing the information is exceedingly useful.

Figure 14:
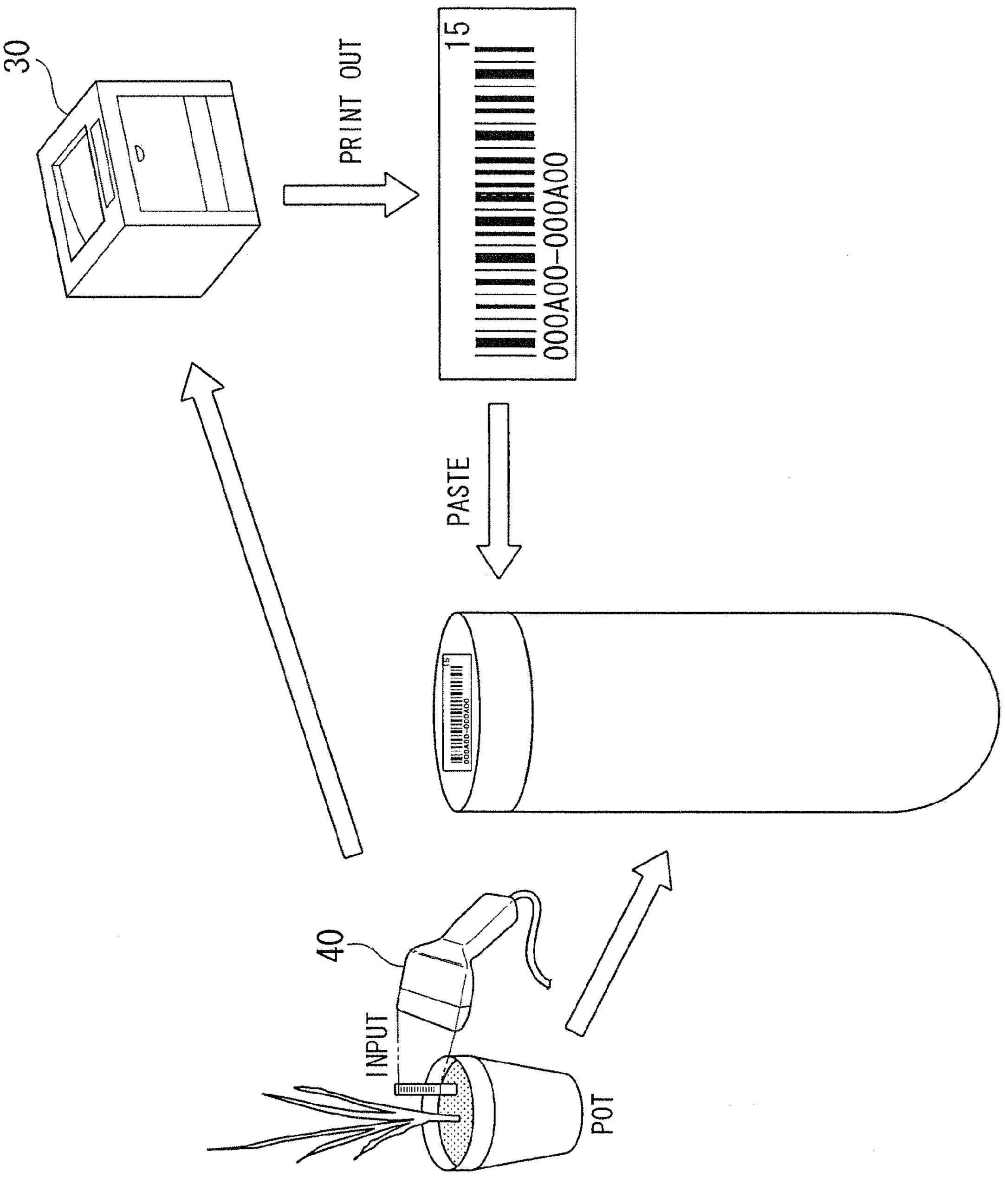
FIG. 14 is a diagram showing part of the user operations in the genetic information analysis procedure.

FIG. 14 shows part of the user processes in the genetic information analysis procedure. When performing the genetic information analysis, the user operates the input device 10 and specifies the individual plant. Thereafter, the user inputs the plant information management system 100 that the genetic information analysis is being operated. The project management device 57, in response to this input, commands the output device 20 to output a screen prompting the user to read the label of the individual plant.

In response to the command, the user operates the label input device 40 and reads the label of the individual plant which is the subject of the genetic information analysis (the "Input" process as shown in FIG. 14). The project management device 57 commands the label output device 30 to print an analysis label representing the individual plant related to the inputted label. In response to the command from the project management device 57, the label output device 30 prints an analysis label (the "Print out" process as shown in FIG. 14). The analysis label includes the individual plant name and the information regarding the culture location.

The user pastes the printed analysis label onto a tissue retrieval container (the "Paste" process as shown in FIG. 14). The user performs tissue sampling from the individual plant to use in an analysis, and puts the sample tissue into the tissue retrieval container on which the analysis label is pasted.

For the tissue retrieval container, standard containers may be used which are widely used in molecular biology and biochemistry experiments, e.g., 15 ml test tubes and 50 ml test tubes. Moreover, DNA extraction and gene analysis can be performed using standard procedures. The user inputs the genetic information obtained from the analysis using the genetic information input device 90 into the plant information management system 100. The seed database management device 55 relates the inputted genetic information to the corresponding seed and records the information onto the seed database. The genetic analysis of the individual plant is not limited to DNA analyses. The individual plant information obtained by genetic analyses may include expression amount and physiological activity of the protein, which are obtained by analyzing the sample tissue using standard procedures. The user may record the protein analysis, and other genetic analysis results in the seed database as well.

In the DNA extraction processes and other standard genetic analysis processes, sample solutions originated from a particular sample tissue are sequentially transferred from one sample tube to another. In such experiment procedures, wherein samples are transferred through different test tubes, by using the same analysis label throughout the experiment, mixing-up of the samples can be avoided. For example, after collecting sample plant tissue, e.g., the leaves, and placing it into the tissue retrieval container, an appropriate buffer solution is added thereto, and a homogenization is performed in order to extract DNA into the buffer from the sample tissue. Thereafter, a centrifugation is performed, and the supernatant including DNA is transferred to a fresh container. After the removal of the supernatant, the user removes the analysis label pasted on the original tissue retrieval container, and pastes the label onto the new container to which the supernatant is transferred. When the analysis label becomes worn out after repeated removal and re-pasting, the user can use the label input device 40 to read the bar-code of the analysis label, and re-issue the same analysis label using the label output device 30. In other words, the user operates the input device 10 to command a re-issuance of the label to the plant information management system 100, and inputs the old analysis label using the label input device 40. The project management device 57, in response to the above described inputs, commands the label output device 30 to print the same analysis label.

Depending on the sample number, if the sample volume is not more than 200 μl, 96-well plates and 384-well plates are commonly used for the sample container. As described above, when the culture plats of the field are labeled corresponding to the labeling of the wells of those containers, analytical samples derived from each individual plant can be analyzed in a well matching the label of the culture location. For example, ten individual plants are cultured in plats "X1A1" to "X1A10" and subjected to a DNA extraction using the leaf tissue thereof. The extracted DNA is subjected to analysis using a 96-well plate designated "X1". The sample derived from the individual plant cultured in the plat X1A1 is placed in well A1, and the sample derived from the individual plant cultured in the plat X1A2 is placed in well A2, and so on. Similarly, the samples are distributed into each matching well of the plate according to each of the culture plat names, and the analysis process is performed. This way, the culture locations and plate wells can be readily matched and mixing-up of the samples during the procedure can be avoided.

According to the plant information management system 100 of the present invention, for seeds of a particular cultivar, the information regarding the parents of the seed and the content of the project to obtain the seed are related to each other and recorded in each of the databases. The information regarding the parents of the seed is recorded in the project database and the seed database. The content of the project are recorded in the project database. The project database and the seed database are related to each other on the basis of the seed name of the offspring obtained by the mating. Therefore, for each managed cultivar's seeds, not only the information regarding the parents thereof, but also the information regarding the procedures which resulted in obtaining the seed is readily retrieved. When the user requires the information regarding the procedures which resulted in further ancestor seed cultivars, the same advantageous effects of efficient information retrieval can be achieved.

Figure 15:
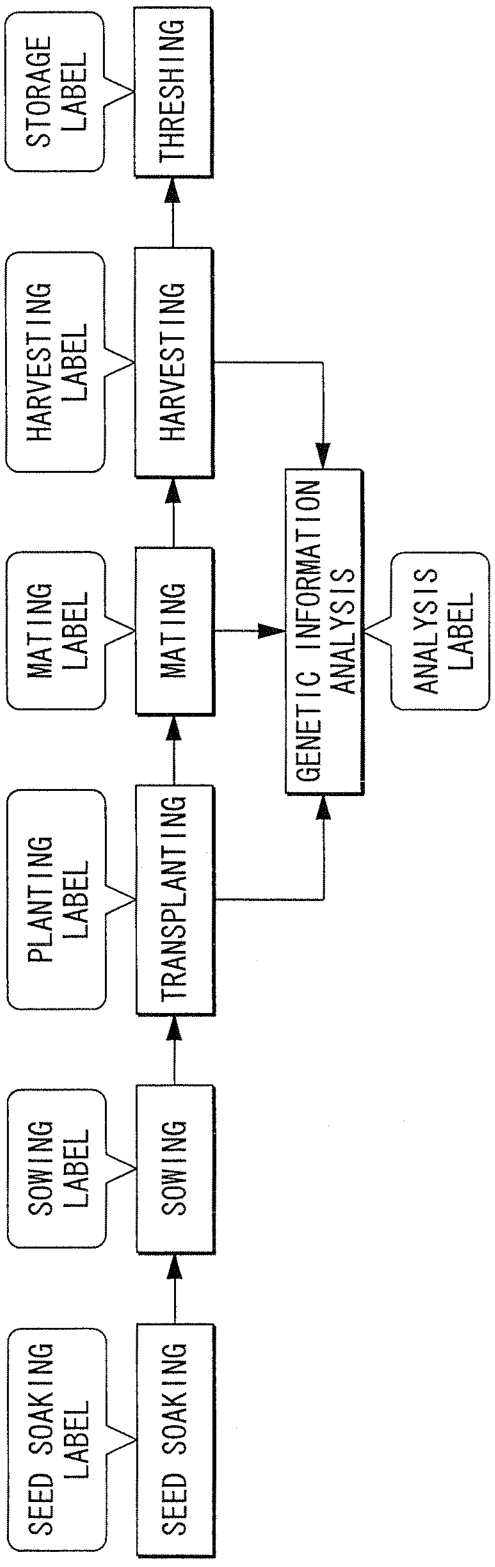
FIG. 15 is a diagram showing the procedures managed by the plant information management system and the labels printed in each of the procedures.

Moreover, according to the plant information management system 100 of the present invention, by the process of the project management device 57, when the user is performing procedures of the project, unless the correct label issued in the previous procedure of the project (i.e., the label pasted on an item related to the particular project) is read by the label input device 40, the label to proceed to the next procedure is not printed. FIG. 15 shows procedures managed by the plant information management system 100 and the labels printed in each of the procedures. The project management device 57 manages the label printing in the each procedure and prints the appropriate label required in the next procedure, as shown in the FIG. 15. Accordingly, the user using an inappropriate seed cultivar, or an inappropriate experiment subject such as an individual plant (i.e., an experiment subject which is irrelevant to the present project) can be avoided as well as proceeding accidentally with the wrong materials in the procedures of the project.

According to the plant information management system 100 of the present invention, in the series of procedures of seed soaking, sowing, transplanting, genetic information analysis, mating, harvesting, and seed storage, mixing-up of the individual plants or seeds can be avoided.

In the plant information management system 100 of the present invention, information regarding self-fertilization may also be managed in addition to the mating information. In this case, the data management of the self-fertilization and the mating can be performed in an integrated manner.

In the present invention, the labels issued are used by pasting on containers or tags. Accordingly, there is a certain extent of limitation in the size of the labels resulting from the size of the object to be pasted thereon. Alternatively, it can be configured so that the labels include text regarding only the most important information, e.g., the name and the culture plat. The remaining information may be printed on the label in the form of barcodes. In this way, the entire individual plant information recorded in the project database can be printed without omission. Moreover, by using the barcode reader, even when the user is in locations such as the culture field and the experiment laboratory, where a direct access to the project database is difficult, the user can readily and quickly obtain the detailed information regarding the individual plant.

Furthermore, for the raising tray and the culture field, by attaching, to the individual plants, transplanting labels including individual plant identification information such as the name of the individual plant, the user can readily identify by sight the kind of plant being cultured therein.

Moreover, in the present invention, analysis labels are pasted on the tissue retrieval containers, each of the analysis labels including the culture location information regarding the individual plant to be sampled. In this case, the sampling from the individual plant can be performed according to the information printed on the analysis label. Accordingly, mixing-up of the individual plants in the sampling procedure can be reduced.

The project database may further include the content of the label printed by the label output device 30 in each of the procedures. In this case, the control section 50 (project database management device 54) records the content of the labels printed by the label output device 30, into the project database.

Part or the entire functions of the plant information management system 100 as described in the above embodiments can be realized by using a computer system. In this case, the program to realize the functions is saved on a recording media readable by the computer system. The program saved on the recording media is loaded onto the computer system, and executed. The "computer system" described above includes an operation system and hardware devices such as peripheral equipment. The "recording media readable by the computer system" includes transportable media such as flexible disks, magneto-optical disks, read-only memory (ROM), and Compact Disc read-only memory (CD-ROM), and hard disk drives installed in the computer system, and other memory devices. The "recording media readable by the computer system" may also include networks such as the internet, and data connections in the case of transmitting programs through telephone circuit, and also includes non-volatile memory in the server and client computers in the above described network, wherein the computer program is dynamically stored therein for a limited amount of time. The program may realize only part of the functions of the embodiment. The program may realize the above described functions in combination with the program already installed on the computer.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A plant information management system comprising:

a seed identification information input device which retrieves a name of a seed to be cultured;

a field database memory device which stores information indicative of an availability of each of a plurality of plats for culturing the seed in connection with at least climate conditions of a culturing field of each plant;

an individual plant identification information retrieval device which retrieves a name of a first individual plant which is produced by germinating the seed;

an individual plant identification information input device which retrieves a name of a second individual plant to be subjected to mating with the first individual plant;

a new seed identification information retrieval device which retrieves a name of a new seed obtained by the mating of the first and the second individual plants and harvested as a head;

a storage location information retrieval device which retrieves information representing a storage location of the new seed;

a project database management device which associates the name of the seed to be cultured, the name of the second individual plant, the name of the new seed, and information regarding a process to obtain the new seed, and records the associated information to a project database;

a seed database management device which associates the name of the new seed, the name of the second individual plant, and information representing the storage location of the new seed, and records the associated information to a seed database;

a project database memory device which stores the project database;

a seed database memory device which stores the seed database;

a project management device which assigns a culture location based on available plats stored in the field database memory, for each of the first individual plant, according to a number of the first individual plant; and a label output device which outputs at least a soaking label and a harvest label, the soaking label having, printed thereon, the name of the seed to be cultured and the culture location, the harvest label having, printed thereon, the name of the new seed and the culture location.

2. The plant information management system according to claim 1, further comprising a genetic information input device which accepts an input of genetic information regarding a seed cultivar, wherein the seed database management device records the genetic information which is inputted to the genetic information input device, into the seed database.

3. The plant information management system according to claim 1, further comprising:

a field database management device which informs to a user whether or not each of the plats is in use, according to a content of the field database memory device; and wherein the field database memory device is configured to store whether each of a plurality of plats for culturing the seed is in use.

4. The plant information management system according to claim 1, further comprising:

a label input device which reads at least a label, wherein:

the project management device instructs the label output device to output the label, in association with a project procedure conducted by the user;

the project database management device stores a content of the label outputted by the project management device and the label output device while relating the content of the label to the project database; and when a first label outputted by the label output device in the project procedure is input by the label input device, the project management device instructs the label output device to output a second label of a next project procedure.

5. The plant information management system according to claim 1, wherein the project database management device manages information regarding the project to obtain the new seed including a planning date, a transplanting date, a heading date, and a harvest date; and the project database management device outputs the information regarding the project database on a display device in response to input from the user.

6. The plant information management system according to claim 1, further comprising an output device which outputs information associated with the seed which is represented by the inputted value by the seed identification information input device, the information being included in the project database and the seed database.

7. A plant information management method comprising the steps of:

acquiring, using a processor, a name of a seed to be cultured;

storing information indicative of an availability of each of a plurality of plats for culturing the seed in connection with at least climate conditions of a culturing field of each plat;

acquiring a name of a first individual plant produced by germinating the seed;

acquiring a name of a second individual plant to be subjected to mating with the first individual plant;

acquiring a name of a new seed obtained by the mating of the first and the second individual plants and harvested as a head;

acquiring a name of a storage location of the new seed;

associating the value representing the seed to be cultured, the name of the second individual plant, the name of the new seed, and a value regarding a project procedure to obtain the new seed, and recording the associated information as a project database;

associating the name of the new seed, the name of the second individual plant, and the storage location of the new seed, and recording the associated information as a seed database;

assigning a culture location based on available plats, for each of the first individual plant, according to a number of the first individual plant; and printing, at least, a soaking label and a harvest label, the soaking label having, printed thereon, the name of the seed to be cultured and the culture location, the harvest label having, printed thereon, the name of the new seed and the culture location.

8. The plant information management method according to claim 7, further comprising the steps of:

acquiring genetic information regarding a seed cultivar; and associating the genetic information with information previously inputted to the seed database and recording the genetic information to the seed database.

9. The plant information management method according to claim 7, further comprising the steps of:

for a plurality of plats to culture the seed, storing whether or not each of the plats is in use; and showing to a user whether or not each of the plats is in use.

10. The plant information management method according to claim 7, further comprising the steps of:

printing a label associated with a project procedure conducted by a user;

associating a content of the label with the information previously recorded to the project database and recording the associated content of the label to the project database;

acquiring an input of the label; and when the label associated with the project procedure is inputted, printing a label associated with a next project procedure.

11. The plant information management method according to claim 7, further comprising the steps of:

recording information regarding the project to obtain the new seed including a planning date, a transplanting date, a heading date, and a harvest date of the project to the project database; and outputting the information in the project database in response to input by a user.

12. The plant information management method according to claim 7, further comprising the step of outputting a plurality of pieces of information related to the seed associated with the inputted value by a user, to the project database and the seed database.

* * * * *